United States Patent [19]

Hosaka

[11] 4,164,333

[45] Aug. 14, 1979

[54] ENDOSCOPE FILM FEEDING DEVICE

[75] Inventor: Kiyokazu Hosaka, Tami, Japan

[73] Assignee: Olympus Optical Company, Tokyo, Japan

[21] Appl. No.: 880,346

[22] Filed: Feb. 23, 1978

[30] Foreign Application Priority Data

Feb. 28, 1977 [JP] Japan .............................. 52/23761[U]

[51] Int. Cl.² ........................ G03B 1/04; G03B 15/14; A61B 1/06
[52] U.S. Cl. ..................................... 242/71.2; 128/6; 242/67.3 R; 354/63
[58] Field of Search ....................... 242/71.2, 71.1, 71, 242/71.3, 71.4, 179, 54 R, 67.3 R, 67.4, 67.1 R, 55; 128/4, 5, 6, 7, 8; 354/62, 63, 212, 214, 213, 215; 33/314; 346/107 W

[56] References Cited

U.S. PATENT DOCUMENTS 3,317,157  5/1967  Leiber .................................. 242/75.5
4,038,977  8/1977  Okada ................................. 242/71.2

Primary Examiner—George F. Mautz

[57] ABSTRACT

An endoscope film feeding device for delivering a film in the distal end portion of a sheath of an endoscope comprises a feeding pulley rotatably mounted in an operation section of the endoscope and having a frusto-conical drum portion with a helical groove in its outer peripheral wall. The feeding device also includes an operating wire with its one end connected to the larger end portion of the drum portion and the other end to a film takeup wire wound about the film takeup pulley in the distal end portion of the sheath. Each time the drum portion is rotated through a predetermined angle, the operating wire gradually engages the helical groove from the larger diameter end to the smaller diameter end so that the operating wire pulls the film takeup wire to rotate the film takeup pulley to feed the film with an equal frame length kept for each film takeup.

4 Claims, 5 Drawing Figures

ENDOSCOPE FILM FEEDING DEVICE

BACKGROUND OF THE INVENTION

This invention relates to a film feeding device for use in an endoscope, which can feed a film toward, and wound around, a film takeup shaft of a film cassette provided in the distal end of an endoscope with an equal frame length kept for each film winding operation.

With conventional endoscopes having a photographing optical system and film housed in its distal end, in general, a feeding pulley of a film feeding device in an operation section is rotated through a predetermined rotation angle, causing an operating wire to be wound around the pulley to permit the film to be fed frame by frame.

In one type of known endoscopes in which a film feeding device permits a film to be drawn toward an operation section of an endoscope, a film can be fed at a relatively equal rate.

In another conventional endoscope in which a film cassette having a film takeup shaft is provided in the distal end of the endoscope, a film is wound around the film takeup shaft. Since the diameter of a film roll on the film takeup shaft is gradually increased as the film is wound about the shaft, the frame length of the film is gradually lengthened and, in consequence, the surplus film portions other than the effective image range are gradually increased, requiring a longer film. In this case, such the surplus portion of the film is not effectively used and, further, a bulkier film cassette is required to hold such a larger rolled film and, in consequence, a correspondingly larger distal end is required for the endoscope. Therefore, a difficulty is encountered in inserting such distal end of the endoscope into a required portion of the coelom or body cavity of a human being.

SUMMARY OF THE INVENTION

An object of this invention is to provide a film feeding device for an endoscope containing in its distal end portion a film cassette having a film takeup shaft and film, and feeding the film frame by frame toward, and wound around, the film takeup shaft with an equal frame length kept for each film takeup operation.

A film feeding device of this invention comprises a film feeding unit disposed within the operation section of an endoscope and including a film feeding pulley having a frustoconical drum portion, and an operating wire having one end connected to a larger diameter end of the drum portion of the film feeding pulley and the other end operatively connected to a film takeup shaft in the distal end of the endoscope, in which when the pulley is rotated through a predetermined angle, the operating wire is wound around the drum portion of the film feeding pulley to cause the film takeup shaft to be rotated. With a continued rotation of the pulley, the operating wire is gradually moved from the larger diameter end to a smaller diameter end of the frustoconical portion of the pulley and, in consequence, the length of a turn around the pulley is gradually decreased. In this way, the film is fed frame by frame toward, and wound around, the film takeup shaft with an equal frame length kept for each film winding operation.

A spiral groove may be provided around the drum portion of the pulley to permit the operating wire to be engaged therewith. In this case, a positive film feeding can also be assured.

DETAILED DESCRIPTION OF THE PREFERRED EMBODIMENT

Figure 2:
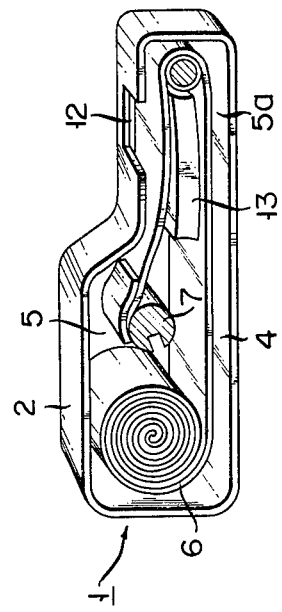
FIG. 2 is a perspective view showing an inner structure of the film cassette of FIG. 1.
Figure 1:
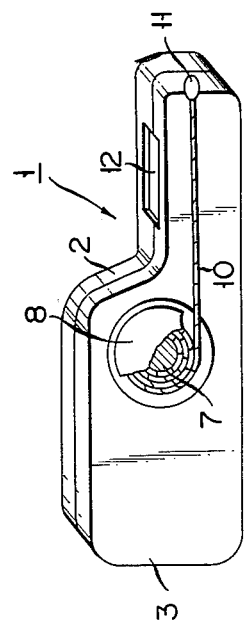
FIG. 1 is a perspective view showing a film cassette adapted to be disposed within the distal end of an endoscope and having a film adapted to be fed and wound by a film feeding device of this invention.

In FIGS. 1 and 2 is shown a film cassette 1 which is disposed within the distal end of an endoscope and has a film fed by a film feeding device. The film cassette 1 comprises a bottomed casing 2 and a cover 3 and includes a film chamber 4 in which a film holding section 5 and exposure section 5a are defined. In the film holding section 5, not only a rolled film 6 is held, but also a takeup shaft 7 is disposed near the exposure section 5a side. The film takeup shaft 7 extends through the cover 3 and has its extending end connected to a film takeup pulley 8 (FIG. 1). A film takeup wire 10 is wound around the pulley 8 in a multi-layer fashion. By pulling the wire 10 away from the film cassette 1 the pulley 8 and takeup shaft 7 are rotated to cause the film 6 to be wound around the shaft 7.

Figure 3:
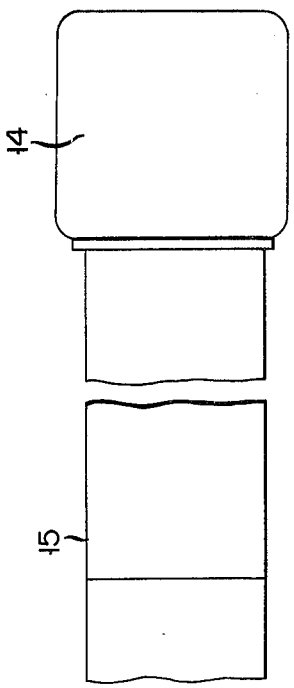
FIG. 3 is a side view of an endoscope whose distal end is partially broken away to show its inner structure and in which there is provided a film feeding device of this invention.

As shown in FIG. 3 a connector 11 is attached to the leading end of the wire 10 and the leading end of the wire 10 can be connected by the connector 11 to the corresponding end of a later described operating wire 9.

An exposure window 12 is provided in a lateral surface of the cassette 1 which is located above the exposure chamber 5a and the cassette 1. The film 6 is guided toward the exposure window 12 by a light-shielding guide member 13. The leading end of the film 6 is held by the takeup shaft 7.

Figure 4:
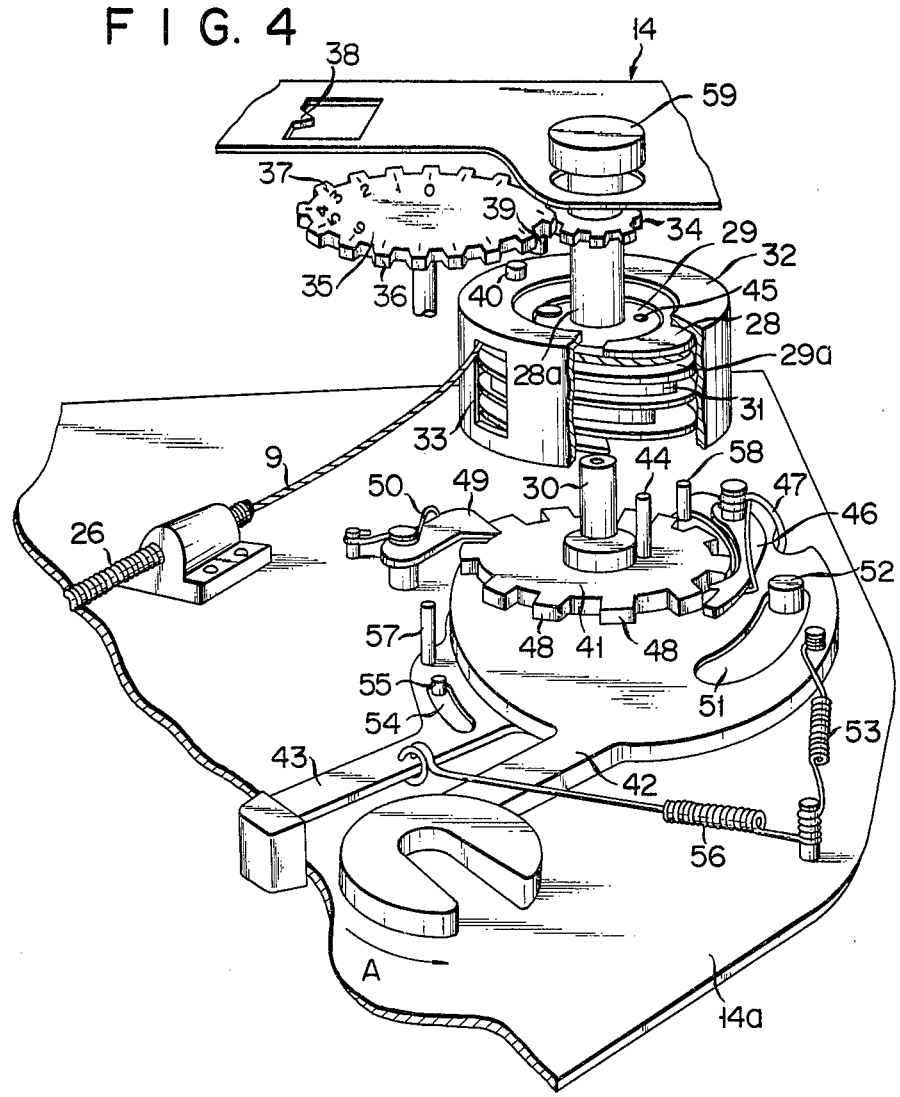
FIG. 4 is a perspective exploded view showing a film feeding device according to one embodiment of this invention.

FIG. 3 is a schematic view showing one embodiment of an endoscope. The endoscope comprises an operation section 14, a flexible sheath 15 and a distal end portion 16. A film cassette holding chamber 17 is defined in the distal end portion 16 and the film cassette 1 is mounted in and detached from the chamber 17 by removing a cap 18 on the distal end portion 16. A photographing optical system 19 is located in that lateral wall portion of the distal end portion 16 which is positioned above the exposure window 12 of the film cassette 1. A photographing window 20 is located in the lateral surface of the distal end portion 16 so as to face the photographing otpical system 19. In the lateral wall of the distal end portion 16, there are provided an observation window 21, an illumination window 22 and an objective optical system 23 disposed inside of the observation window 21. A bundle 24 of image guide optical fibers extends through the flexible sheath 15 such that one end of the bundle 24 is located at the focus of the objective optical system 23 and the other end is connected to an ocular portion or eyepiece (not shown) at the operation section 14. A bundle 25 of light guiding optical fibers in the flexible sheath 15 extends between the illumination window 22 and a light source optically connected to the optical section 14. A flexible tube 26 extends from the operation section 14 to the rear end portion of the distal end portion 16 and an operating wire 9 is inserted through the flexible tube 26. A connector 27 is connected to the front end of the operating wire 9. The connector 27 is connected to the connector of the wire 10 and, in consequence, the wires 9 and 10 are connected to each other. The other end of the wire 9 is wound around a film feed pulley 28 (FIG. 4). The shaft 28a of the pulley 28 is rotatably mounted on a shaft 30 fixed to a body 14a of the operation section 14. A drum section 29 is frustoconical and has a helical blade member 29a provided around the outer peripheral surface thereof at an equal pitch. The outer periphery surface of the drum section 29, together with the helical blade member 29a, provides a spiral or helical groove or helical engaging portion 31 which the operating wire 9 engages. The drum section 29 is set to have a predetermined tapered surface as will be later described. The pulley 28 is surrounded by a cylindrical casing or cover 32 to prevent the wire 9 from being removed from the helical groove 31 of the pulley 28 while the wire 39 is unwound or after the connector 11 is disengaged from the connector 27. In consequence, the inner surface of the casing 32 is located in close proximity to the outer peripheral surface of the pulley 28 so that the spiral groove 31 is blocked. An opening 33 is provided in the side wall of the casing 32 to permit the wire 9 to tangentially engage the helical groove 31.

A toothed wheel 34 is fixed on the shaft 28a of the pulley 28. The wheel 34 engages a teeth 36 on the outer peripheral surface of a frame number indicating disc 35. The rotation of the pulley 28 is transmitted by the wheel 34 to the frame number indicating disc 35 to cause the latter to be rotated. A fixed mark 38 on the operation section 14 points at one of scales 37 on the frame number indicating disc 35 to permit the number of unexposed film frames to be read therefrom. A pin 39 projects from the disc 35 toward the top surface of the cover 32 and a stop 40 projects from the top surface of the casing 32 toward the disc 35. When the disc 35 is rotated through a predetermined angle, the pin 39 abuts against the stop 40 to prevent further rotation of the disc 35. A ratchet 41, takeup lever 42 and release lever 43 are separately pivotally mounted on the shaft 30.

An engaging pin 44 projects from the ratchet 41 toward the pulley 28. The pin 44 is inserted into an engaging hole 45 of the pulley 28 and in consequence the ratchet 41 and pully 38 are rotated as a unit. A ratchet pawl 46 is pivoted on the takeup lever 42 and urged, by a spring 47, to engage one of teeth 48 of the ratchet 41. When the takeup lever 42 is rotated in a direction indicated by an arrow A in FIG. 4 the ratchet pawl 46 is disengaged from the ratchet 41. When the winding lever 42 is rotated reversely, the ratchet pawl 46 engages the ratchet 41 to cause the latter to be rotated clockwise through substantially the same angle as the lever 42. A detent pawl 49 is pivotally mounted on a body 14a of the operation section 14 and is urged, by a spring 50, to engage one of the teeth 48 of the ratchet 41 so as to prevent the ratchet 41 to be rotated in the direction A.

An arcuate guide hole 51 is formed in the takeup lever 42. A stop pin 52 is fixed on the body 14a of the operation section 14 and penetrates the hole 51. The takeup lever 42 can be rotated through an angle range in which the stop pin 52 abuts against the extreme edges of the hole 51. The takeup lever 42 is urged by a spring 53 in the direction in which the ratchet pawl 46 engages the tooth 48 of the ratchet 41 (that is, in the opposite direction to the arrow A). An arcuate guide hole 54 is provided in the release lever 43 and a stop pin 55 projects from the body 14a of the operation section 14 into the arcuate guide hole 54. The release lever 43 is urged by a spring 56 in the direction of the arrow A in FIG. 4 and can be rotated in the direction opposite to that in which the takeup lever 42 is rotated against the spring 56. A pair of pins 57, 58 project from the release lever 43. When the release lever 43 is rotated clockwise against the urging force of the spring 56, the pins 57 and 58 engage the detent pawl 49 and ratchet pawl 46, respectively, to cause both the pawls 49, 46 to be moved away from the teeth 48 of the ratchet 41. The takeup lever 42 and release lever 43 can be operated from outside the operation section 14 of the endoscope.

The upper end of the shaft 28a of the pulley 28 extends out from the operation section 14 and is fixed by a knob 59. When the pawls 46, 49 are disengaged from the teeth 48 of the ratchet 41 by the clockwise rotation of the release lever 43, the pulley 28 can be freely rotated by the knob 59.

In operation, the takeup lever 42 is rotated in the direction A (that is, counterclockwise) against the urging force of the spring 53 until the stop pin 52 abuts against the extreme right edge the arcuate guide hole 51. As a result, the ratchet pawl 46 clears a ratchet tooth 48 most recently engaged therewith and engages with the next adjacent ratchet tooth 48. When the takeup lever 42 is released, it is returned by the spring 53 to the original position as shown in FIG. 4. At this time, the ratchet 41 is clockwise rotated by one ratchet tooth. While the ratchet 41 is rotated clockwise, the pulley 28 is also clockwise rotated by the pin 44 through the same angle as the ratchet 41 is to cause the operating wire 9 to be wound on the spiral groove 31 of the pulley 28. When the operating wire 9 is wound so around the pulley 28, the wire 10 wound around the pulley 8 of the film cassette 1 in the distal end 16 of the endoscope is drawn out by a corresponding amount. At this time, the pulley 8 and thus the shaft 7 is rotated to cause the film 6 to be fed one frame and, in consequence, the frame is located above the exposure window 12. After the film is photographed, the above-mentioned film winding operation is repeated and the film is fed frame by frame for exposure and photographing. During the film winding operation the wire 9 is wound on the helical groove 31 of the pulley 28. As the winding of the wire 9 on the helical groove 31 of the pulley 28 continues, the diameter of the spiral groove 31 is gradually decreased. In consequence, the length of one turn around the helical groove 31 becomes shorter than that of the preceding one turn around the helical groove 31 of the pulley 28. Thus the length of the takeup wire 10 which is pulled toward the pulley 28 is gradually shortened as the takeup operation is repeated. Apart from this construction of the pulley 28, suppose that the pulled length of the wire 10 is unchanged each time the film is taken up. As the takeup of the film 6 around the shaft 7 in the cassette 1 continues, the diameter of the roll of the film 6 on the shaft 7 is increased. Thus, even if shaft 7 is rotated through an equal angle each time the film is taken up, the length of one frame of the film 6 is gradually increased. In reality, however, as the takeup of the film 6 around the shaft 7 continues, the diameter of a roll of the wire 10 on the pulley 8 is gradually decreased with the result that the rotation angle of the shaft 7 is gradually increased. Thus, the film length per frame is more lengthened as the film takeup operation is repeated.

In the embodiment of this invention, the length of one turn around the helical groove 31 of the pulley 28 is shorter than the preceding one turn around the helical groove 31 of the pulley 28, and in consequence the rotation angle of the shaft 7 can be decreased. If, therefore, the drum portion 29 of the pulley 26 is selected to have a proper tapered surface, a constant feed rate can be always obtained for each film winding operation.

When the fixed mark 38 indicates the "0" scale on the disc 35, the pin 39 on the disc 35 abuts against the stop 40 on the cylindrical cover 32, thereby preventing any further film winding operation.

The exposed film can be removed as follows:

When the release lever 43 is rotated clockwise, the pins 57 and 58 engage the detent pawl 49 and ratchet pawl 46, respectively, causing the pawls 49, 46 to be moved away from the teeth 48 of the ratchet 41. As a result, the ratchet 41 can be freely rotated. Then, the cap 18 is removed from the distal end 16 of the endoscope and the film cassette 1 is taken out of the film cassette holding chamber 17 of the distal end portion 16 of the endoscope. The wire 9 connected to the wire 10 is drawn out from the distal end portion 16, since the ratchet 41 can be freely rotated. Outside the distal end portion 16 of the endoscope, the connector 11 of the wire 10 is removed from the connector 21 of the wire 9 and the cassette 1 is completely detached from the distal end portion 16.

Figure 5:
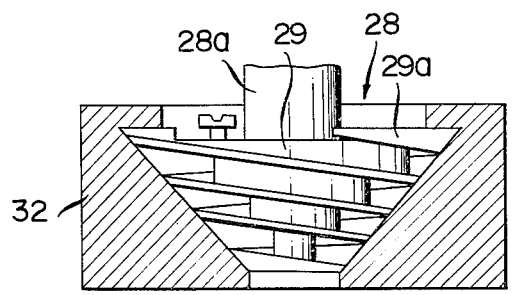
FIG. 5 shows a film feeding pulley according to another embodiment of this invention.

FIG. 5 shows a film feed pulley 28 according to another embodiment of this invention. The film feed pulley 28 includes a helical blade member 29a having the outer edge forming a conical configuration. A cover or casing 32 has an inner concial surface complementary to the outer conical configuration of the helical blade member 29a. Such a combination of the pulley 28 and cover 32 prevents the wire 9 from being dropped out of the helical blade member 29a of the pulley 28. The other reference numerals given to the parts of the pulley 28 are identical to those of the corresponding parts of the embodiment of FIG. 4 and further explanation is therefore omitted.

What is claimed is:

1. A film feeding device used in an endoscope for pulling a film takeup wire wound around a film takeup pulley of a film cassette placed in a distal end of the endoscope comprising:
    a shaft rotatably mounted on a body of an operation section of the endoscope;
    a generally frustoconical drum portion fixedly mounted on the shaft;
    a helical blade member formed on an outer periphery of the drum portion;
    a casing covering the drum portion and having an inner surface complementary to a shape defined by the outer periphery of the blade member, said casing having an axially elongated opening formed in a lateral wall thereof;
    an operating wire connected at one end to the larger diameter end of the drum portion and that portion succeeding to said one end which is engaged with a groove defined by the outer periphery of the drum portion and the blade member, said operating wire having an intermediate portion passing through the opening which extends through the endoscope, with the other end of the operating wire detachably connected by the film takeup wire; and
    a knob fixed on a free end of the shaft for rotating the drum portion in either direction.

2. The device according to claim 1, wherein the inner surface of said casing and said shape defined by the outer periphery of said blade member are cylindrical.

3. The device according to claim 1, wherein the inner surface of said casing and said shape defined by the outer periphery of said blade member are frustoconical.

4. The device according to claim 1, further including a ratchet-pawl assembly comprising a ratchet provided coaxially with the drum portion and rotated therewith, and pawls pivotally mounted on the body of the operation section for restricting the rotational angle of the ratchet and the drum portion.

* * * * *